US006999549B2

(12) United States Patent
Sabol et al.

(10) Patent No.: US 6,999,549 B2
(45) Date of Patent: Feb. 14, 2006

(54) METHOD AND APPARATUS FOR QUANTIFYING TISSUE FAT CONTENT

(75) Inventors: John Michael Sabol, Sussex, WI (US); Matthew Joseph Walker, New Berlin, WI (US); Gopal B. Avinash, New Berlin, WI (US); Kadri Nizar Jabri, Waukesha, WI (US)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 266 days.

(21) Appl. No.: 10/306,052

(22) Filed: Nov. 27, 2002

(65) Prior Publication Data

US 2004/0101086 A1    May 27, 2004

(51) Int. Cl.
*A61B 6/00*     (2006.01)
*G01N 23/087*   (2006.01)

(52) U.S. Cl. ............................................ 378/5
(58) Field of Classification Search .................. 378/5
See application file for complete search history.

(56) References Cited

U.S. PATENT DOCUMENTS

| 4,029,963 | A | | 6/1977 | Alvarez et al. |
| 4,157,472 | A | | 6/1979 | Beck, Jr. et al. |
| 4,361,901 | A | | 11/1982 | Daniels et al. |
| 4,957,729 | A | * | 9/1990 | Counsell et al. ......... 424/9.451 |
| 5,115,394 | A | | 5/1992 | Walters |
| 5,155,365 | A | * | 10/1992 | Cann et al. .................... 378/5 |
| 5,570,403 | A | | 10/1996 | Yamazaki et al. |
| 5,665,971 | A | | 9/1997 | Chen et al. |
| 6,018,562 | A | | 1/2000 | Willson |
| 6,185,272 | B1 | | 2/2001 | Hiraoglu et al. |
| 6,236,709 | B1 | | 5/2001 | Perry et al. |
| 6,320,931 | B1 | | 11/2001 | Arnold |
| 6,369,389 | B1 | | 4/2002 | Berlad et al. |
| 6,418,189 | B1 | | 7/2002 | Schafer |
| 6,501,819 | B2 | * | 12/2002 | Unger et al. .................... 378/5 |
| 6,507,633 | B1 | * | 1/2003 | Elbakri et al. ................. 378/8 |
| 6,560,315 | B1 | | 5/2003 | Price et al. |
| 6,898,263 | B2 | * | 5/2005 | Avinash et al. ................. 378/4 |
| 2002/0163988 | A1 | | 11/2002 | Nisius et al. |
| 2003/0063787 | A1 | | 4/2003 | Natanzon et al. |
| 2004/0101104 | A1 | | 5/2004 | Avinash et al. |

OTHER PUBLICATIONS

Duncan, et. al. "The use of dilute Calogen® as a fat density oral contrast medium in upper abdominal computed tomography, compared with the use of water and positive oral contrast media" Clinical Radiology (2001) 56: 670-673.*

Madden et al. "The potential role of dual-energy x-ray absorptiometry in the assessment of body composition in cirrhotic patients" Nutrition vol. 13, No. 1, pp 40-45.*

What is nonalcoholic fatty liver (NAFL)/ nonalcoholic steatohepatitis (NASH)? American Liver Foundation 2001.*

Stephen J. Swensen et al., Lung Nodules: Dual-Kilovolt Peak Analysis with CT-Multicenter Study, Radiology, Jan. 2000.

Mini Pandit-Bhalla, MD, Dual Kilovolt of Solitary Pulmonary Nodules: Importance of Equipment Calibration and Soft-Tissue Controls, Radiology, Jan. 2001, 214: 81-85.

(Continued)

*Primary Examiner*—Craig E. Church
*Assistant Examiner*—Krystyna Suchecki
(74) *Attorney, Agent, or Firm*—Carl B. Horton, Esq.; Armstrong Teasdale LLP

(57) ABSTRACT

A method for obtaining data includes quantifying tissue fat content using a multi-energy computed tomography (MECT) system.

21 Claims, 6 Drawing Sheets

OTHER PUBLICATIONS

Fatty Liver, Gastroenterology Consultants, PC, http://www.gastro.com/html/liverdisease/fatty_liver.shtml, American Liver Foundation, 1995.

Tsutomo Douchi et al., Inverse relationship between the changes in trunk lean and fat mass during gonadotropin-releasing hormone agonist therapy, Maturitas 42 (2002) 31-35.

H Fors et al., Body composition, as assessed by bioelectrical impedance spectroscopy and dual-energy X-ray absorptiometry, in a healthy paediatric population, Acta Paediatr 91.

R.J. Bolt et al., Body composition in infants with chronic lung disease after treatment with dexamethasone, Acta Paediatr 91: 815-821, 2002.

John M. Boone, PhD, et al., Dedicated Breast CT: Radiation Dose and Image Quality Evaluation, Radiology, Dec. 2001, 221: 657-667.

Ruola Ning et al., Flat panel detector-based cone beam volume CT breast imaging, preliminary phantom study, Medical Imaging 2001, Physics of Medical.

Henry J. Goldberg et al., Noninvasive Quantification of LIver Iron in Dogs with Hemochromatosis Using Dual-Energy CT Scanning, Investigative Radiology. Jul.-Aug. 1982.

Vassilios Rartopoulos et al., Value of Dual-Energy CT in Differentiating Focal Fatty Infiltration of the Liver from Low-Density Masses, AJR: 157, Oct. 1991.

B. Wang et al., Quantitative Diagnosis of Fatty Liver With Dual-Energy CT, Acta Radiologica 44 (2003) 92-97.

Michel-Henry Mendler et al., Dual Energy CT in the diagnosis and quantification of fatty liver, Journal of Hepatology 1998; 28; 785-794.

P.M. Braillon, Annual Changes in Bone Mineral Content and Body Composition during Growth, Horm. Res. 2003; 60; 284-290.

P.M. Braillon et al., Contenu Mineral Osseux et Composition Corporelle au Cours de la Croissance: Quantification par Absorptiometrie a Rayons X, J Radiol 2002: 83.

* cited by examiner

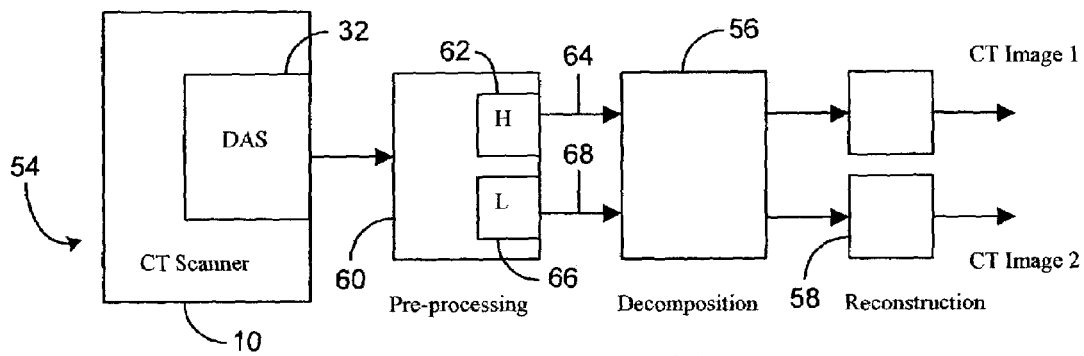
Figure 3. Pre-reconstruction Analysis
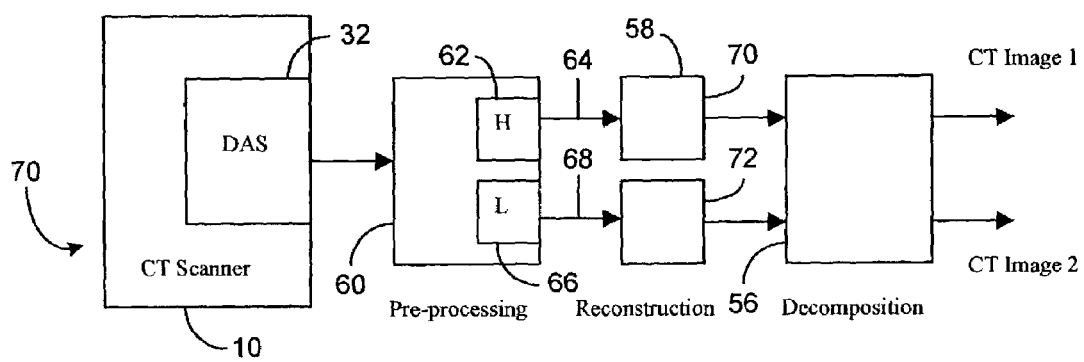
Figure 4. Post-reconstruction Analysis

METHOD AND APPARATUS FOR QUANTIFYING TISSUE FAT CONTENT

BACKGROUND OF THE INVENTION

This invention relates generally to medical imaging systems, and more specifically to a method and apparatus for quantifying tissue fat content using a medical imaging system.

In spite of recent advancements in computed tomography (CT) technology, such as faster scanning speed, larger coverage with multiple detector rows, and thinner slices, energy resolution is still a missing piece. Namely, a wide x-ray photon energy spectrum from the x-ray source and a lack of energy resolution from CT detection systems preclude energy discrimination CT.

X-ray attenuation through a given object is not a constant. Rather, x-ray attenuation is strongly dependent on the x-ray photon energy. This physical phenomenon manifests itself in an image as a beam-hardening artifact, such as non-uniformity, shading, and streaks. Some beam-hardening artifacts can be easily corrected, but others may be more difficult to correct. In general, known methods to correct beam hardening artifacts include water calibration, which includes calibrating each CT machine to remove beam hardening from materials similar to water, and iterative bone correction, wherein bones are separated in the first-pass image then correcting for beam hardening from bones in the second-pass. However, beam hardening from materials other than water and bone, such as metals and contrast agents, may be difficult to correct. In addition, even with the above described correction methods, conventional CT does not provide quantitative image values. Rather, the same material at different locations often shows different CT numbers.

Another drawback of conventional CT is a lack of material characterization. For example, a highly attenuating material with a low density can result in the same CT number in the image as a less attenuating material with a high density. Thus, there is little or no information about the material composition of a scanned object based solely on the CT number. Additionally, detection of fat within tissues is often difficult because the images produced by such scanners may exhibit a significant level of image artifacts and CT number inaccuracy. These limitations may prevent the utilization of the CT device for advanced diagnosis. For example, some normal and pathological biological processes result in accumulation of higher levels of fat within an organ or tissue. In some cases, the fat can be readily detected by imaging or physical examination. In other cases, the fat is distributed throughout normal tissue in varying amounts, possibly making detection of the distributed fat difficult.

An example of fat distributed throughout normal tissue is the accumulation of fat in liver cells, herein referred to as a fatty liver. A fatty liver is typically not considered a disease because it does not damage the liver, however, a fatty liver is symptomatic of a number of pathological processes including, for example, tuberculosis, diabetes mellitus, extreme weight gain, alcoholism, poor diet, intestinal bypass surgery for obesity, and the use of certain drugs such as corticosteroids. Known methods for diagnosing a fatty liver include microscopically examining a sample of liver tissues obtained from biopsy of the liver. In addition, both a bright ripple pattern as seen on an ultrasound image of a liver, and reduced density as seen on an x-ray computed tomography (CT) image of a liver, may suggest the presence of a fatty liver. Furthermore, fatty liver patients may have an enlarged liver or have isolated minor elevation of liver enzymes as measured by routine blood screening. However, a definitive diagnosis of a fatty liver is typically determined by microscopically examining liver tissue samples obtained from an invasive liver biopsy procedure.

BRIEF DESCRIPTION OF THE INVENTION

In one aspect, a method is provided for obtaining data. The method includes quantifying tissue fat content using a multi-energy computed tomography (MECT) system.

In another aspect, a multi-energy computed tomography (MECT) system is provided including at least one radiation source, at least one radiation detector, and a computer operationally coupled to the radiation source and the radiation detector. The computer is configured to receive data regarding a first energy spectrum of a scan of an object including tissue, receive data regarding a second energy spectrum of the scan of the tissue, and decompose and segment the received data to identify regional fatty tissue and lean tissue.

In a further aspect, a multi-energy computed tomography (MECT) system is provided including at least one radiation source, at least one radiation detector, and a computer operationally coupled to the radiation source and the radiation detector. The computer is configured to receive image data for tissue, decompose the image data into a first density map representative of fatty tissue and a second density map representative of lean tissue, and merge said first density map with said second density map.

In yet another aspect, a computer readable medium embedded with a program is provided. The computer readable medium is configured to instruct a computer to receive data regarding a first energy spectrum of a scan of tissue, receive data regarding a second energy spectrum of the scan of the tissue, decompose the received data to generate a first density map representative of fatty tissue and a second density map representative of lean tissue, merge the first density map with the second density map to generate a fat/lean ratio map, and segment the merged first and second density map to determine a region of interest.

In even yet another aspect, a computer is provided that is configured to receive MECT image data for tissue, and decompose and segment the image data into a first density map representative of fatty tissue within a region of interest and a second density map representative of lean tissue within a region of interest.

BRIEF DESCRIPTION OF THE DRAWINGS

FIG. 3 is a flow chart representing a pre-reconstruction analysis.

FIG. 4 is a flow chart representing a post-reconstruction analysis.

DETAILED DESCRIPTION OF THE INVENTION

Figure 1:
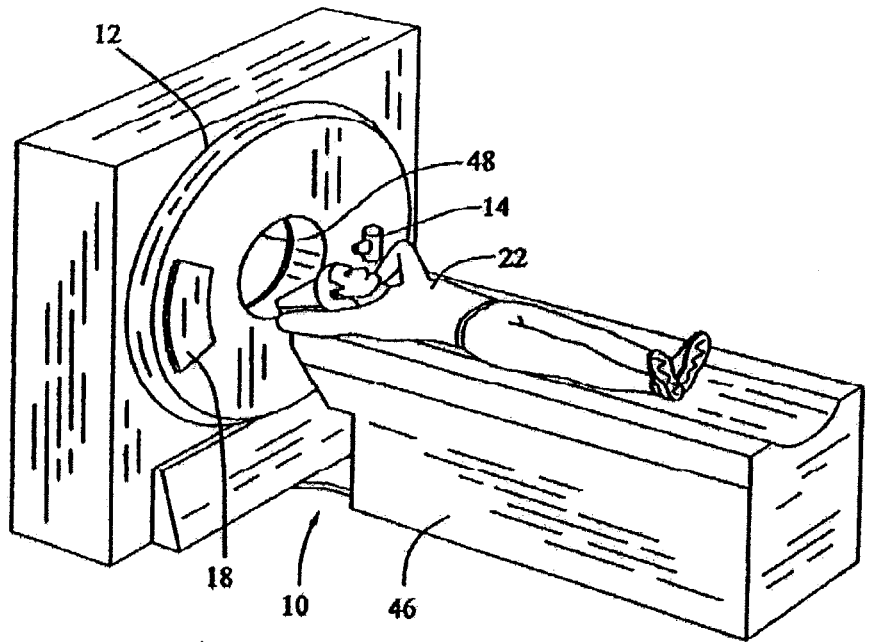
FIG. 1 is a pictorial view of a MECT imaging system.

The methods and apparatus described herein facilitate accurate, non-invasive, inexpensive, and a definitive diagnosis of a fatty liver, and facilitate quantifying the tissue fat content in other organs and regions of a body. The methods and systems described herein may be used to determine the fat content, or relative fat content of any tissue or organ, in any animal, tissue specimen, or human. Additionally, the methods described herein include novel approaches to make use of the basic properties of the x-ray and material interaction. For example, for each ray trajectory, multiple measurements with different mean x-ray energies are acquired. When BMD and/or Compton and photoelectric decomposition are performed on these measurements, additional information is obtained that may facilitate improved accuracy and characterization. For example, one such characterization is determination of fat content for each voxel of acquired data. Local determination of tissue fat content facilitates improving the specificity of understanding about the composition and metabolic function of the tissue in question. Furthermore, a combination of fat-based contrast agents may facilitate a wide variety of new diagnostic examinations, and may facilitate reducing the invasiveness of existing procedures.

In some known CT imaging system configurations, an x-ray source projects a fan-shaped beam which is collimated to lie within an x-y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view." A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed, wherein the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the methods and systems described herein are not intended to be interpreted as excluding the existence of additional embodiments that also incorporate the recited features.

Also as used herein, the phrase "reconstructing an image" is not intended to exclude embodiments of the methods and systems described herein in which data representing an image is generated but a viewable image is not. However, many embodiments generate (or are configured to generate) at least one viewable image.

Herein are described methods and apparatus for quantifying tissue fat content using an energy-discriminating (also known as multi-energy) computed tomography (MECT) system. First described is MECT system 10 and followed by contrast applications using MECT system 10.

Figure 2:
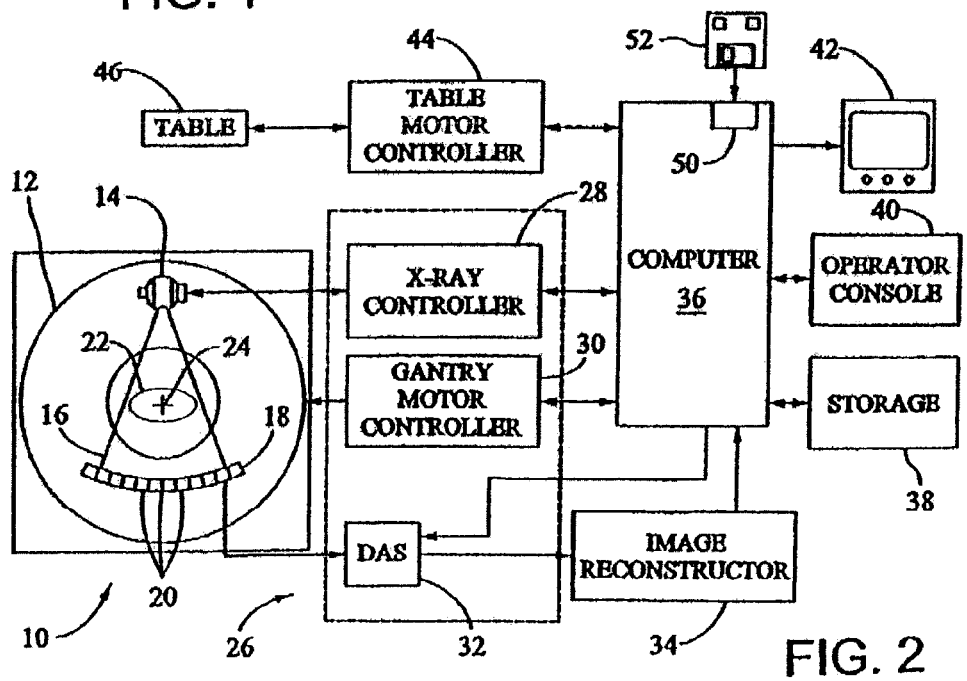
FIG. 2 is a block schematic diagram of the system illustrated in FIG. 1.

Referring to FIGS. 1 and 2, a multi-energy scanning imaging system, for example, a multi-energy multi-slice computed tomography (MECT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, micro-controllers, microcomputers, programmable logic controllers, application specific integrated circuits, and other programmable circuits, and these terms are used interchangeably herein. CT imaging system 10 is an energy-discriminating (also known as multi-energy) computed tomography (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials, for example. Alternatively, special filters are placed between the x-ray source and the detector such that different detector rows collect projections of different x-ray energy spectrum. Alternatively, the special filters that shape the x-ray spectrum can be used for two scans that are acquired either back to back or interleaved. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source).

There are different methods to obtain multi-energy measurements, (1) scan with two distinctive energy spectra, (2) detect photon energy according to energy deposition in the detector, and (3) photon counting. Photon counting provides clean spectra separation and an adjustable energy separation point for balancing photon statistics.

MECT facilitates reducing or eliminating a plurality of problems associated with conventional CT, such as, but not limited to, a lack of energy discrimination and material characterization. In the absence of object scatter, one only need system 10 to separately detect two regions of photon energy spectrum, the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation, (1) Compton scatter and the (2) photoelectric effect. Thus, detected signals from two energy regions provide sufficient information to resolve the energy dependence of the material being imaged. Furthermore, detected signals from two energy regions provide sufficient information to determine the relative composition of an object composed of two materials.

In an exemplary embodiment, MECT uses a decomposition algorithm, such as, but not limited to, a CT number difference algorithm, a Compton and photoelectric decomposition algorithm, a basis material decomposition (BMD) algorithm, or a logarithm subtraction decomposition (LSD) algorithm.

The CT number difference algorithm includes calculating a difference value in a CT or a Hounsfield number between two images obtained at different tube potentials. In one embodiment, the difference values are calculated on a pixel-by-pixel basis. In another embodiment, average CT number differences are calculated over a region of interest. The Compton and photoelectric decomposition algorithm includes acquiring a pair of images using MECT 10, and separately representing the attenuations from Compton and photoelectric processes. The BMD algorithm includes acquiring two CT images, wherein each image represents the equivalent density of one of the basis materials. Since a material density is independent of x-ray photon energy, these images are approximately free of beam-hardening artifacts. Additionally, an operator can choose the basis material to target a certain material of interest, thus enhancing the image contrast. In use, the BMD algorithm is based on the concept that the x-ray attenuation (in the energy region for medical CT) of any given material can be represented by proper density mix of other two given materials, accordingly, these two materials are called the basis materials. In one embodiment, using the LSD algorithm, the images are acquired with quasi-monoenergetic x-ray spectra, and the imaged object can be characterized by an effective attenuation coefficient for each of the two materials, therefore the LSD algorithm does not incorporate beam-hardening corrections. Additionally, the LSD algorithm is not calibrated, but uses a determination of the tissue cancellation parameters, which are the ratio of the effective attenuation coefficient of a given material at the average energy of each exposure. In an exemplary embodiment, the tissue cancellation parameter is primarily dependent upon the spectra used to acquire the images, and on any additional factors that change the measured signal intensity from that which would be expected for a pair of ideal, mono-energetic exposures.

It should be noted that in order to optimize a multi-energy CT system, the larger the spectra separation, the better the image quality. Also, the photon statistics in these two energy regions should be similar, otherwise, the poorer statistical region will dominate the image noise.

The methods and systems described herein apply the above principle to tissue characterization. In specific, MECT system 10 is utilized to produce CT images as herein described. Pre-reconstruction analysis, post-reconstruction analysis and scout image analysis are three techniques that can be used with MECT system 10 in performing tissue characterization.

FIG. 3 is a flow chart representing a pre-reconstruction analysis 54 wherein a decomposition 56 is accomplished prior to a reconstruction 58. Computer 36 collects the acquired projection data generated by detector array 18 (shown in FIG. 1) at discrete angular positions of the rotating gantry 12 (shown in FIG. 1), and passes the signals to a preprocessor 60. Preprocessor 60 re-sorts the projection data received from computer 36 to optimize the sequence for the subsequent mathematical processing. Preprocessor 60 also corrects the projection data from computer 36 for detector temperature, intensity of the primary beam, gain and offset, and other deterministic error factors. Preprocessor 60 then extracts data corresponding to a high-energy view 62 and routes it to a high energy channel path 64, and routes the data corresponding to a low-energy views 66 to a low energy path 68. Using the high energy data and low energy data, a decomposition algorithm is used to produce two streams of projection data, which are then reconstructed to obtain two individual images pertaining to two different materials.

FIG. 4 is a flow chart representing a post-reconstruction analysis wherein decomposition 56 is accomplished after reconstruction 58. Computer 36 collects the acquired projection data generated by detector array 18 (shown in FIG. 1) at discrete angular positions of rotating gantry 12 (shown in FIG. 1), and routes the data corresponding to high-energy views 62 to high energy path 64 and routes the data corresponding to low-energy views 66 to low energy path 68. A first CT image 70 corresponding to the high-energy series of projections 62 and a second CT image 72 corresponding to low-energy series of projections 66 are reconstructed 58. Dual-energy decomposition 56 is then performed using a decomposition algorithm to obtain two individual images respectively, pertaining to two different materials. In scout image analysis, the signal flow can be similar to FIG. 3 or FIG. 4. However, the table is moved relative to the non-rotating gantry to acquire the data.

The use of dual energy techniques in projection x-ray imaging may facilitate diagnosing and monitoring osteoporosis, and determining an average fat-tissue to lean-tissue ratio (fat/lean ratio). Dual energy techniques may also facilitate cross-sectional or tomographic x-ray imaging for osteoporosis detection in human subjects, and may facilitate non-destructive testing applications, for example explosive and/or contraband detection.

When tissue characterization is performed using radiographic imaging, for example bone-mineral density measurement, only an average tissue thickness (in the basis material decomposition description) along the projection path is determined. Furthermore, using multi-energy imaging, a measured thickness of a given material may depend upon accurate estimation of the attenuation of the complementary material for multiple energy spectra. For example, accurate measurement of bone mineral density may require accurate determination of the soft-tissue attenuation along the x-ray path traversing the bone being investigated, and therefore may limit the application of such techniques to medical applications. In addition, and for example, a fat lean ratio can be determined for a sample of ground beef wherein it is assumed that the fat and lean components are homogeneously mixed through the sample, and/or that sufficient sampling is undertaken to average over variations in fat and lean distribution. Accordingly, a fat lean ratio may be determined for a human or animal subject, if the assumption of uniform and/or homogeneous mixing applies. However, if a fat-lean ratio for a specific organ and/or region of the body is desired, assuming uniform and/or homogeneous distribution may not be valid.

Figure 5:
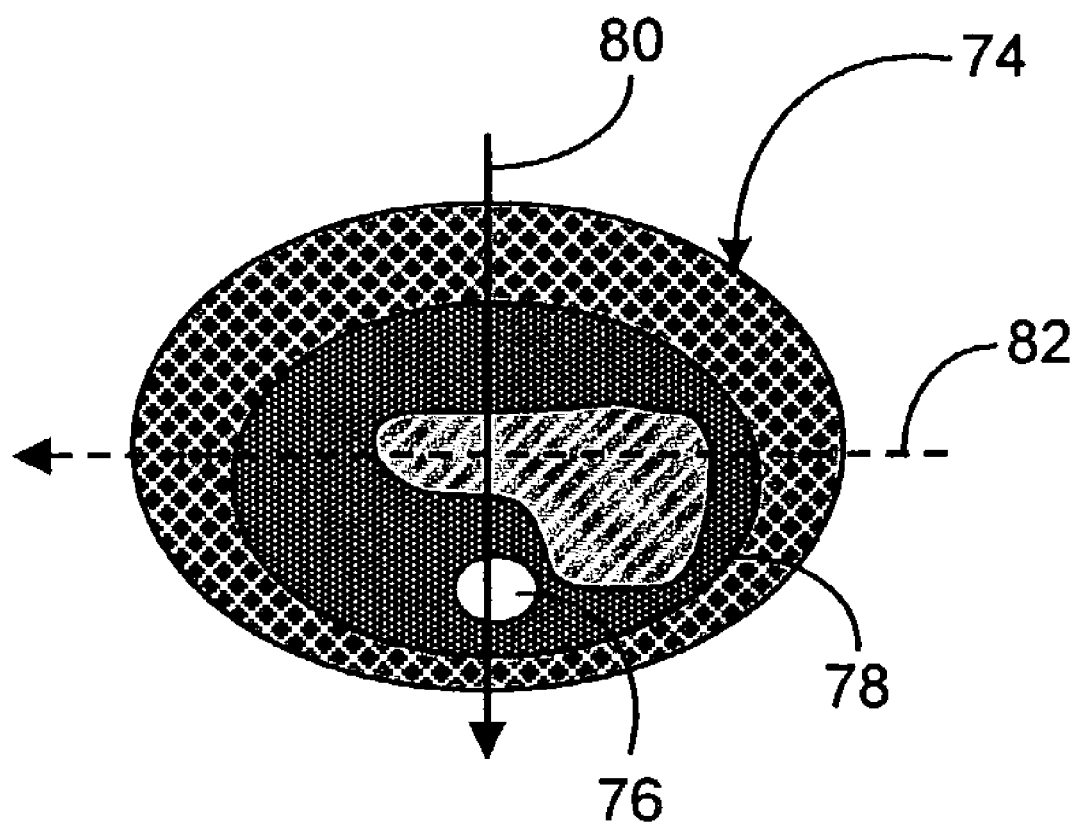
FIG. 5 is a schematic illustration of tissue including subcutaneous fat and an organ of interest.

For example, FIG. 5 is a schematic illustration of tissue 74 including sub-cutaneous fat 76 and an organ of interest 78. A first projection 80 and a second projection 82 register different fat contents within tissue 74, and more specifically outside organ 78, due to an irregular distribution of sub-cutaneous fat 76 within tissue 74. Thus, if varying amounts of fat are present along a projection path, then different assessments of percent fat in an organ may be obtained due only to a variation in the fat-lean ratios outside the organ of interest.

The methods and systems described herein take advantage of tomographic capabilities of CT imaging geometry to overcome prior limitations and make a variety of tissue characterizations that may not be possible using projection radiographic techniques. In addition, the methods and systems described herein may be used to determine the fat content, or relative fat content of any tissue or organ, in any animal, tissue specimen, or human.

Figure 6:
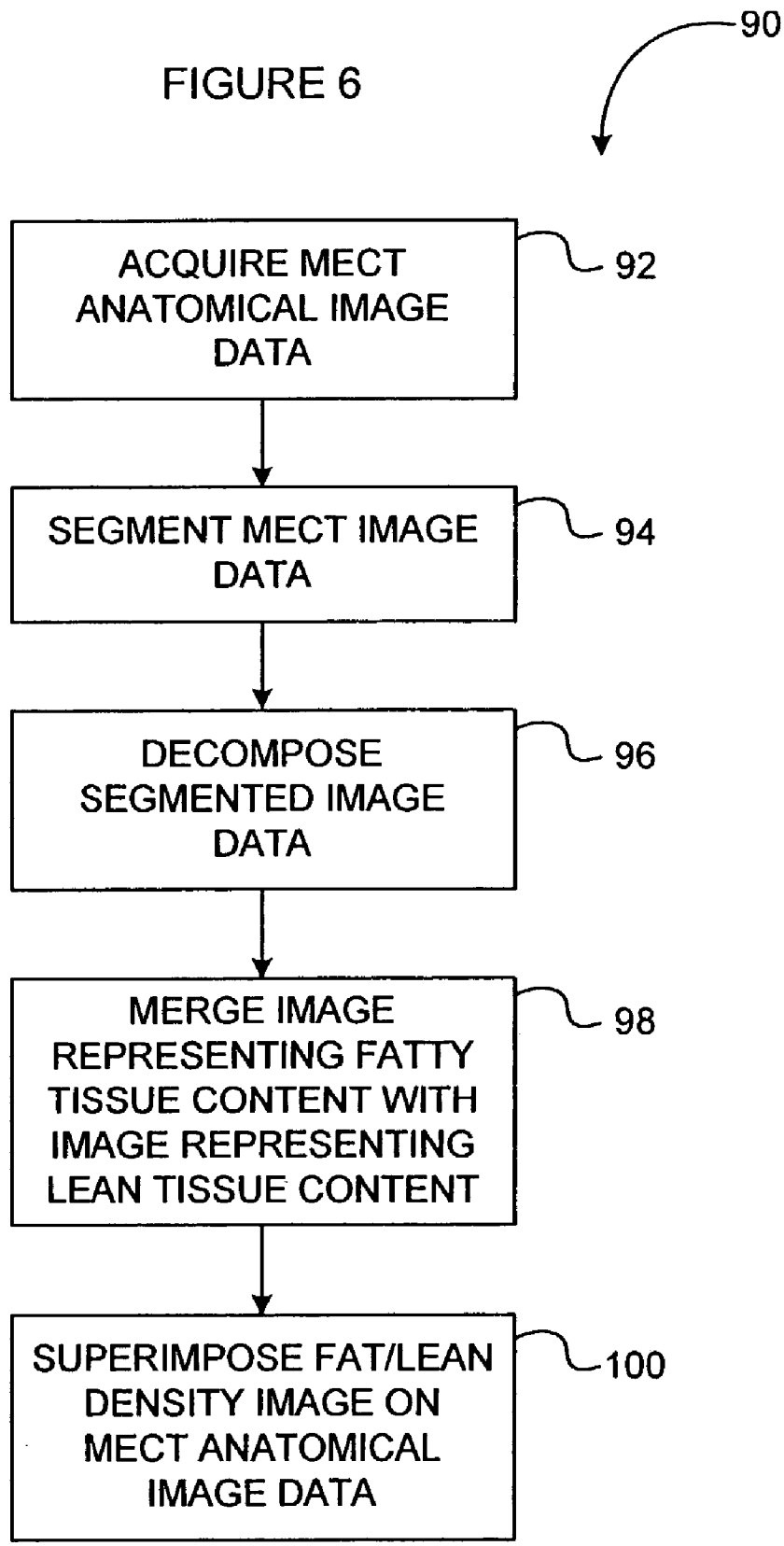
FIG. 6 is a schematic illustration of a method for quantifying tissue fat content in tissue using the MECT imaging system illustrated in FIGS. 1 and 2.

FIG. 6 is a schematic illustration of a method 90 for quantifying fat content in tissue 74 (shown in FIG. 5) using MECT system 10 (shown in FIGS. 1 and 2). Method 90 utilizes a priori anatomical information to perform a local, targeted, image acquisition and/or reconstruction of a smaller-than normal field of view to segment a region of interest from surrounding tissues. In one embodiment, CT images are segmented using various techniques including Hounsfield or CT number (threshold) techniques, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, and neural networks. Accordingly, any calculations performed on projection data will reflect attenuation variations from within the field-of-view. In one embodiment, the a priori anatomical information is purely anatomical information derived from either measurements or landmarks supplied by an individual controlling the acquisition process. In another embodiment, a priori anatomical information is image-based and derived from a scout view image, a plurality of scout view images, or previous images from a CT or another modality, for example magnetic resonance imaging (MRI), electron beam tomography (EBT), ultrasound, positron emission tomography (PET), and x-ray.

In use, method 90 includes acquiring 92 MECT anatomical image data for tissue 74, and segmenting 94 the MECT image data to determine a region of interest, for example an organ of interest such as a liver. Once the region of interest is segmented 94 from the surrounding region of tissue, such as tissue 74, a tissue characterization is determined for the region of interest. More specifically, the segmented image data is decomposed 96 to obtain a density image representing a content of fatty tissue within the region of interest and a density image representing a content of lean tissue within the region of interest. The image representing fatty tissue content is then merged 98 with the image representing lean tissue content to obtain a density image that quantifies on a pixel by pixel basis a fat/lean ratio for every point within the region of interest. In one embodiment, the anatomical image is displayed conventionally (gray-scale corresponding to CT numbers) while the fat/lean density image may then be superimposed 100 on the anatomical image to obtain a combined image for the region of interest. More specifically, the fatty tissue image and the lean tissue image are registered with each other and the pixel values of the fatty tissue image are divided by the pixel values of the lean tissue image on a pixel by pixel basis.

Figure 7:
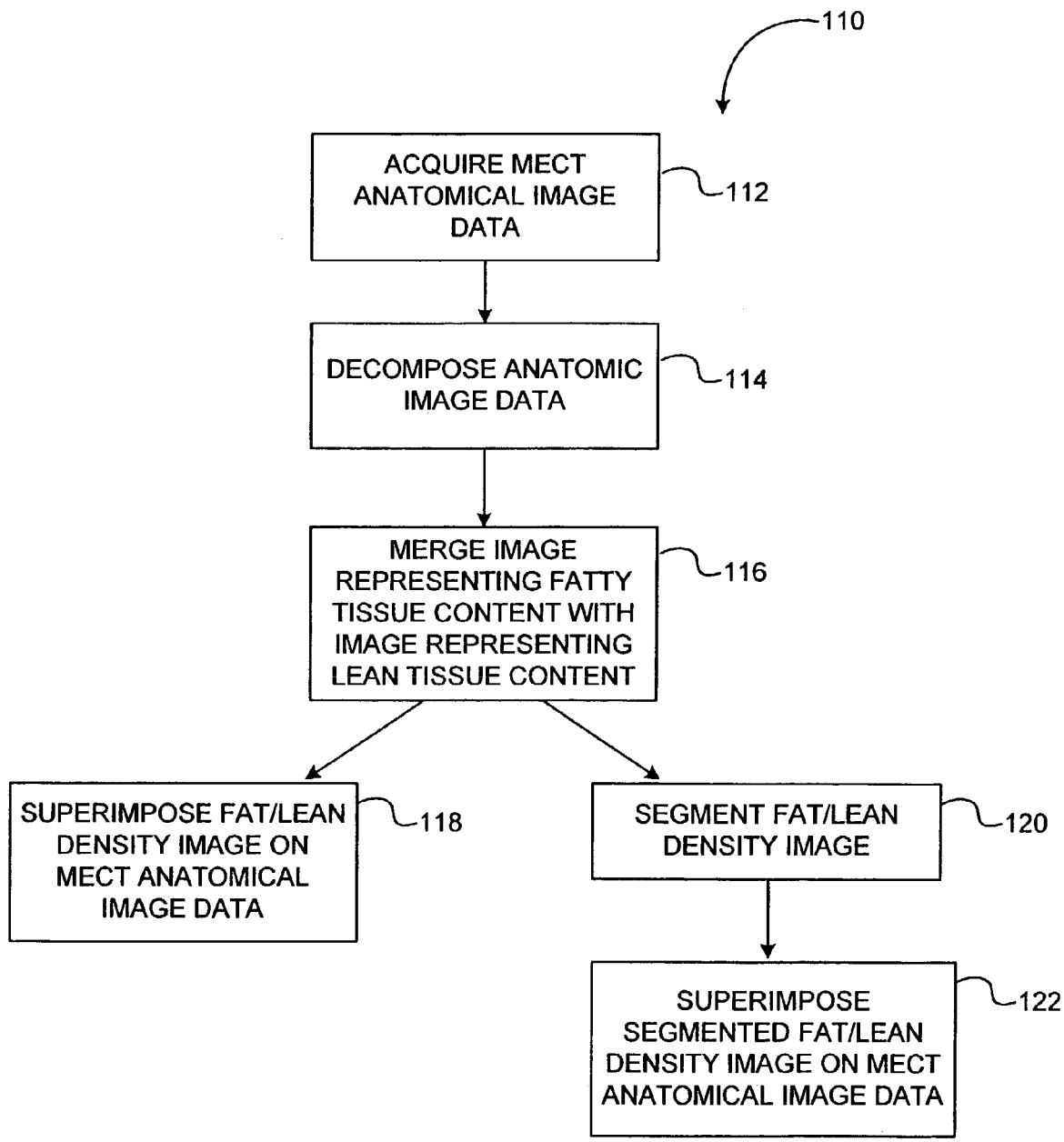
FIG. 7 is a schematic illustration of a method for quantifying tissue fat content in tissue using the MECT imaging system illustrated in FIGS. 1 and 2.

FIG. 7 is a schematic illustration of a method 110 for quantifying fat content in tissue 74 (shown in FIG. 5) using MECT system 10 (shown in FIGS. 1 and 2). Method 110 utilizes segmentation of an image field to determine a region-of-interest for tissue characterization. Decomposed images are segmented using the above described CT image segmentation techniques. In one embodiment, segmentation of a region of interest is performed manually. Manual segmentation of a region of interest includes displaying image data to a user, wherein the user delineates the region using a mouse or any other suitable interface, such as, for example, a touch screen, eye-tracking, and/or voice commands. In an alternative embodiment, segmentation of a region of interest is performed automatically. Automated segmentation of a region of interest includes using an algorithm that automatically delineates an area of interest using prior knowledge, such as the shape and size of a mass. In yet another embodiment, segmentation of a region of interest is performed using a combination of manual and automatic segmentation.

In use, method 110 includes acquiring 112 MECT anatomical image data for tissue 74, and decomposing 114 the anatomical image data to obtain a density image representing a content of fatty tissue within tissue 74 and a density image representing a content of lean tissue within tissue 74. The image representing fatty tissue content is then merged 116 with the image representing lean tissue content to obtain a density image that quantifies on a pixel by pixel basis a fat/lean ratio for every point within tissue 74. More specifically, the fatty tissue image and the lean tissue image are registered with each other and the pixel values of the fatty tissue image are divided by the pixel values of the lean tissue image on a pixel by pixel basis. In one embodiment, the fat/lean density region is superimposed 118 on the MECT anatomical image data to obtain a combined image for tissue 74. In an alternative embodiment, the fat/lean density image is first segmented 120 to determine a region of interest, for example an organ of interest such as a liver. Once the region of interest is segmented 120 from the surrounding region of tissue 74, then a tissue characterization can be determined for the region of interest. More specifically, the segmented fat/lean density image may then be superimposed 122 on the MECT anatomical image data to obtain a combined image for the region of interest.

Figure 8:
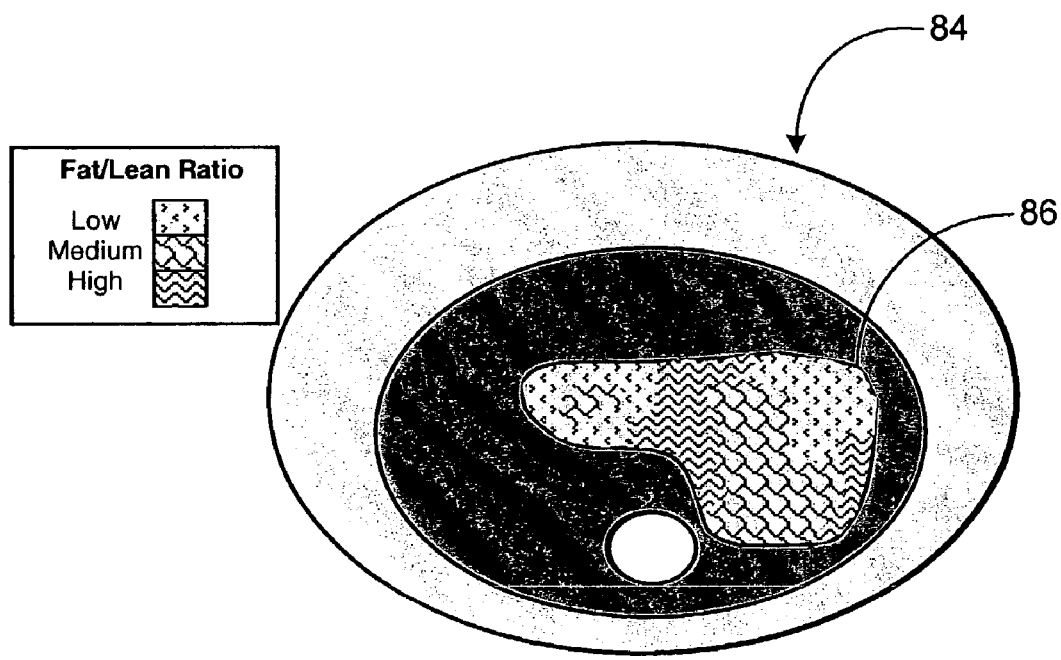
FIG. 8 is a schematic illustration of tissue showing regional fat/lean ratios in regions of interest.

FIG. 8 is a schematic illustration of tissue 84 showing a fat/lean ratio in a region of interest 86, for example a liver. In the exemplary embodiment illustrated in FIG. 8, tissue characterization data is displayed using a grayscale display to depict the morphological characteristics of the imaged anatomy, in the same way that conventional CT images are displayed. The grayscale value is linked to the CT number through an appropriate look-up table. This morphological component of the displayed data can be chosen from any one of the MECT image data sets, or a combination of two or more. In the exemplary embodiment, a texture pattern overlay indicative of local fat content is superimposed on the morphological data. In an alternative embodiment, a color overlay indicative of local fat content is superimposed on the morphological data. In this manner both the CT number (grey level) and fat content (texture or color pattern) may be simultaneously displayed to an observer. In one embodiment, the observer can toggle between the two views (anatomical and characteristic), or toggle the addition of the overlay, via software switch(es).

In use, the methods described herein facilitate improving the contrast between fatty and normal tissue by performing a decomposition using the above described decomposition techniques. Additionally, the methods described herein facilitate reducing image artifacts by improving beam-hardening correction. Improved beam-hardening correction may increase accuracy of the tissue characterization, and may avoid the appearance of shading and streaking artifacts, which decrease the ability of an observer to visualize fatty-normal tissue characteristics and can significantly change the local CT number and hence the accuracy of tissue characterization. Accordingly, the methods described herein may facilitate reducing image artifacts, improving CT number accuracy, and improving tissue characterization.

In addition, the methods described herein facilitate the ability to perform tissue characterization. Using the principle of BMD, there may be an increased probability that different diseased tissues can be classified and separated, for example fatty liver characterization and total percent body fat measurements. Furthermore, the methods described herein facilitate detection and staging of fatty liver and similar conditions using automated and semi-automated quantitative analysis of MECT images. Computer-aided detection (CAD) and/or computer-aided diagnosis (CADx) algorithms can take advantage of the tissue characterization, in addition to the morphological information presented by the image datasets. Accordingly, providing MECT images as inputs to CAD/CADx algorithms provides more information than single-energy images.

The methods described herein may also facilitate the staging and treatment monitoring of diseases or conditions that are characterized by changes in body fat. Furthermore, local changes in the fat-lean tissue ratio in patients may be assessed with MECT. For example, the stage of a disease, or treatment, may be assessed and monitored with either a single scan or by utilizing multiple scans over time and measuring changes in the fat-lean tissue content. Temporal analysis of stored MECT images is performed by human observers or computer algorithms (CAD/CADx), or a combination of the two methods.

Additionally, the methods described herein also facilitate characterization of the fat-lean content of breast tissue in a MECT data acquisition of a breast. Such a MECT data acquisition may be conducted in a standard CT geometry, with the patient lying supine on an examination table, or on a dedicated breast CT system. Furthermore, the methods described herein may facilitate monitoring a wide variety of biological processes when used in combination with contrast agents. The contrast agents could be as simple as ingested dietary fat (for example, to monitor the ingestion, digestion, and absorption of fat in the gastro-intestinal system following consumption of a high fat meal), or a complex targeted contrast agent composed of a fat or lipid compound. Such contrast agents can be minimally invasive, and much less toxic than conventional iodinated contrast agents.

The above-described methods and systems facilitate enabling new clinical applications for a variety of disease conditions, and facilitate the ability of CT scanning to diagnose, stage, and monitor the treatment of fatty liver and other diseases. Additionally, the above-described methods include new types of information that may be acquired using CT scanning, and facilitate offering the potential for greater use of CT in molecular imaging applications using tissue characterization. Furthermore, the above-described methods and systems may facilitate opening new medical markets for CT applications using tissue characterization, including fat/ lean ratio quantification, and may facilitate enabling development of new, non-invasive, bio-compatible contrast agents and examinations.

Exemplary embodiments of MECT methods and systems are described above in detail. The methods and systems are not limited to the specific embodiments described herein, but rather, components of each method and system may be utilized independently and separately from other components described herein. In addition, each method and system component can also be used in combination with other components described herein.

While the invention has been described in terms of various specific embodiments, those skilled in the art will recognize that the invention can be practiced with modification within the spirit and scope of the claims.

What is claimed is:

1. A method for obtaining data, said method comprising performing at least one scout scan, acquiring x-ray multi-energy computed tomography (MECT) image data, automatically segmenting the MECT image data using a priori anatomical information derived from at least one scout scan to determine a region of interest, decomposing the MECT image data into a first density map representative of fatty tissue and a second density map representative of lean tissue to quantify tissue fat content in the region of interest, and using said quantified tissue fat content to detect a clinical condition in the region of interest.

2. A method in accordance with claim 1 wherein decomposing the MECT image data comprises decomposing the MECT image data using at least one of a CT number difference decomposition, a Compton and photoelectric decomposition, a basis material decomposition (BMD), and a logarithm subtraction decomposition (LSD).

3. A method in accordance with claim 1 further comprising merging the first density map with the second density map to obtain a density image that quantifies fat content.

4. A method in accordance with claim 3 wherein merging the first density map with the second density map comprises generating a fat/lean ratio map on a pixel by pixel basis between the merged first and second density maps.

5. A method in accordance with claim 4 further comprising superimposing the ratio map on an anatomical image of the tissue.

6. A method in accordance with claim 5 wherein superimposing the ratio map further comprises displaying the ratio map in color as an overlay to a grayscale anatomical image of the tissue.

7. A method in accordance with claim 3 further comprising segmenting the merged first and second density maps to determine a region of interest.

8. A method in accordance with claim 7 wherein segmenting the merged first and second density maps comprises segmenting the merged first and second density maps using at least one of pixel-value thresholding, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, and neural networks.

9. A method in accordance with claim 7 wherein segmenting the merged first and second density maps comprises manually segmenting the merged first and second density maps using displayed image data.

10. A method in accordance with claim 7 wherein segmenting the merged first and second density maps comprises automatically segmenting the merged first and second density maps using an algorithm.

11. A multi-energy computed tomography (MECT) system comprising:
at least one x-ray radiation source;
at least one x-ray radiation detector; and
a computer operationally coupled to said radiation source and said radiation detector, said computer configured to:
receive data regarding at least one scout scan of a patient;
receive data regarding a first energy spectrum of an x-ray computed tomography scan of tissue of the patient;
receive data regarding a second energy spectrum of an x-ray computed tomography scan of the tissue;
decompose and segment said received data to identify regional fatty tissue and lean tissue, wherein said segmenting comprises automatic segmentation using a priori anatomical information derived from the at least one scout scan to identify a region of interest in the tissue;
use said identification of regional fatty and lean tissue to detect a clinical condition in the tissue.

12. A MECT system in accordance with claim 11 wherein the tissue is liver tissue, and said computer configured to use said identification of regional fatty and lean tissue to detect a clinical condition in the tissue further comprises said computer configured to use said identification of regional fatty and lean tissue to detect a fatty liver condition.

13. A MECT system in accordance with claim 12 wherein said computer configured to decompose said received data using at least one of a CT number difference decomposition, a Compton and photoelectric decomposition, a basis material decomposition (BMD), and a logarithm subtraction decomposition (LSD).

14. A MECT system in accordance with claim 12 wherein said computer further configured to:
decompose said received data to generate a first density map representative of fatty tissue and a second density map representative of lean tissue; and
merge said first density map with said second density map to generate a fat/lean ratio map on a pixel by pixel basis between said first and second density maps.

15. A MECT system in accordance with claim 14 wherein said computer further configured to superimpose said fat/lean ratio map on an anatomical image of the tissue.

16. A MECT system in accordance with claim 13 wherein said computer further configured to:
said computer further configured to:
create a first density map representative of fatty tissue and a second density map representative of lean tissue;
merge said first density map with said second density map; and
said using said identification of regional fatty and lean tissue further comprises using fatty tissue and lean tissue characterizations to detect a fatty liver condition.

17. A MECT system in accordance with claim 11 wherein said computer configured to segment said merged first and second density map using at least one of pixel-value thresholding, an iterative thresholding, a k-means segmentation, an edge detection, an edge linking, a curve fitting, a curve smoothing, a 2D/3D morphological filtering, a region growing, a fuzzy clustering, image/volume measurements, a heuristic, knowledge-based rules, decision trees, and neural networks.

18. A computer readable medium embedded with a program configured to instruct a computer to:
receive data regarding at least one scout scan of a patient;

receive data regarding a first energy spectrum of an x-ray multi-energy computed tomographic (MECT) scan of tissue including a liver;

receive data regarding a second energy spectrum of an x-ray scan of the tissue;

decompose said received data to generate a first density map representative of fatty tissue and a second density map representative of lean tissue;

merge said first density map with said second density map to generate a fat/lean ratio map;

automatically segment said merged first and second density map using a priori anatomical information derived from the at least one scout scan to determine a region of interest; and use fatty tissue and lean tissue characterizations to detect a fatty liver condition.

19. A computer readable medium in accordance with claim 18 wherein said computer readable medium configured to instruct the computer to decompose said received data using at least one of a CT number difference decomposition, a Compton and photoelectric decomposition, a basis material decomposition (BMD), and a logarithm subtraction decomposition (LSD).

20. A computer configured to:

receive data regarding at least one scout scan of a patient;

receive an x-ray MECT image data for tissue;

decompose and segment said image data into a first density map representative of fatty tissue within a region of interest and a second density map representative of lean tissue within a region of interest, wherein said segmenting comprises automatic segmenting using a priori anatomical information derived from said at least one scout scan of the patient; and decompose and segment said image data to thereby identify a contrast agent consisting of ingested dietary fat.

21. A method for obtaining data, said method comprising performing at least one scout scan to acquire scout image data, obtaining x-ray MECT image data, and, based upon information derived from the scout scan, segmenting and decomposing the x-ray MECT image data into a first density map representative of fatty tissue and a second density map representative of lean tissue to quantify tissue fat content in the region of interest, and using said quantified tissue fat content to detect a clinical condition in the region of interest.

* * * * *

UNITED STATES PATENT AND TRADEMARK OFFICE
CERTIFICATE OF CORRECTION

PATENT NO. : 6,999,549 B2 Page 1 of 1
APPLICATION NO. : 10/306052
DATED : February 14, 2006
INVENTOR(S) : Sabol et al.

It is certified that error appears in the above-identified patent and that said Letters Patent is hereby corrected as shown below:

In Claim 18, column 13, line 5, between "x-ray" and "scan" insert -- MECT --.

Signed and Sealed this

Nineteenth Day of August, 2008

JON W. DUDAS
*Director of the United States Patent and Trademark Office*